US00PP09025P

United States Patent [19]

McRae

[11] Patent Number: Plant 9,025

[45] Date of Patent: Dec. 27, 1994

[54] LILIUM 'PINK PEONY'

[75] Inventor: Judith F. McRae, Boring, Oreg.

[73] Assignee: Mt. Hood Lilies, Inc., Sandy, Oreg.

[21] Appl. No.: 238,030

[22] Filed: May 4, 1994

[51] Int. Cl.[5] ..... A01H 5/00

[52] U.S. Cl. ..... Plt./87.4

[58] Field of Search ..... Plt. 87.4

References Cited

[56] U.S. PATENT DOCUMENT p.p. 7,161 2/1990 McRae ..... plt./87.4

*Primary Examiner*—James R. Feyrer

[57] ABSTRACT

A new variety of hybrid lily plant bearing large, upfacing, double pink flowers of excellent form and long persistence. The double flowers of the new hybrid have uniquely "notched" tepals, and they are borne on exceptionally short, sturdy stems. This combination is completely new in the Asiatic hybrid divisions of lilies suited to forcing and to mass commercial cultivation for use as pot plants. The variety is highly resistant to fusarium disease and shows tolerance of virus. The bulbs may be precooled and forced into flower under glass out of season. The clone is vigorous and is a good grower and propagator.

1 Drawing Sheet

BACKGROUND OF THE INVENTION

My new variety of lily plant originated as a seedling which first flowered in Boring, Oreg. in 1988. The breeding efforts had as their objective the production of truly short Asiatic lilies with large, attractively double flowers in shades of pink and peach, suited to forcing into flower out of season for pot plants, heretofore unknown in the lily breeding art.

I achieved the desired objective by pollinating Lilium 'China' (U.S. Plant No. 7,161) with pollen from an unnamed genetically short seedling with peach-salmon flowers which often produced semi-double flowers. The pollen parent was unique to my own breeding lines and was never released.

The flowers of my new lily are characterized by an upfacing orientation, large size, pink color, and a consistently double form frequently accentuated by "notched" tepals, which creates a more ruffled effect. The buds are unusually broad, and the stems are exceptionally short. In addition, the clone possesses to a high degree desirable characteristics of hybrid vigor. The clone is a good grower and propagator, as observed at Boring, Oreg.

My new variety of lily plant has been asexually reproduced by me and under my direction at Boring, Oreg. Successive generations produced by natural propagation from bulblets, bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawings, which show the open bloom in full color and illustrate in particular the novel and distinctive double flower form with its uniquely "notched" tepals, the unusually wide buds, and the exceptionally short stems.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of the Royal Horticultural Society, published by the Society in 1966.

THE PLANT

Origin: Seedling.

Seed parent: Lilium 'China' (U.S. Plant Pat. No. 7,161).

Pollen parent: Unnamed genetically short seedling with semi-double peach-salmon flowers.

Commercial classification: Hybrid Lilium clone.

Horticultural classification: Division IA, Upfacing Asiatic hybrid lily, according to the Horticultural Classification of Lilies, Royal Horticultural Society of London.

Form: Single stem, erect and stately.

Height: 20 to 45 cm from bulbs 14 to 18 cm in circumference, provided their light levels are adequate; low light levels may cause "stretching."

Growth: Vigorous and upright.

Foliage quantity: Abundant.

Size of leaf: 10 to 15 cm long×0.75 to 2 cm wide.

Shape of leaf: Lanceolate (pointed).

Texture: Leathery and glossy.

Color: Medium to dark green, lighter on lower side.

Bulb size: Any size, ranging to 25 cm circumference commmercially.

Bulb color: White, with flushes of pink or yellow after exposure to light.

THE BUD

Form: Obtuse, ovoid, and long.

Size: 8 to 10 cm long and 8 to 12 cm in circumference just prior to opening.

Opening: Bud opens slowly, in response to morning light; this takes about one hour.

Color: RHS CC red-purple 62 C-D, with green midribs, just prior to opening.

Peduncle: Average 1–3 cm, but it may elongate if light levels are too low or if bulbs have been improperly stored prior to forcing. Color is deep green.

THE FLOWER

Blooming habit: Annually in midseason; flowers once and profusely.

Size: Flowers are large-sized, averaging 14 to 18 cm in diameter, reflexing at the tips on the second day to 12–16 cm in diameter. The tepals vary in width, but the outermost tepals average 2.25 to 3 cm wide.

Borne: In a single racemic inflorescene producing 4 to 10 flowers from a bulb 12 to 16 cm in circumference; 10 to 12 cm bulbs produce 2–4 flowers in a more umbellate inflorescence.

Shape: Consistently double flowers, typically with 10 to 18 tepals per flower. Some flowers show fewer tepals, but all stems produce fully double flowers. Inner tepals may not be as broad as the outer tepals, but they often have a conspicuous "notch" which creates a greater "ruffing" effect.

Tepalage: 10 to 18 imbricated tepals, varying from flower to flower.

Tepal color: RHS CC red 55 C/D to red-purple 62 A-C, lighter along midribs. Color is more intense when grown with bright illumination and moderate temperatures. Bulbs forced under lower light conditions produce flowers slightly lighter and less purple-pink than those grown with full illumination.

Tepal spotting: Most flowers are spotless, but some flowers show a few inconspicuous spots at the base of the tepals only.

Tepal longevity: Tepals stay on stems about three weeks.

Pedicel length: Average 4 to 8 cm long.

Pedicel color: Dark green with light purple overlay.

Pedicel form: Sturdy and slightly ascending.

Color changes: Flowers become slightly lighter as the flowers age. Low light levels and extreme heat will reduce color intensity.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting.

THE REPRODUCTIVE ORGANS

Stamens: Most flowers have no stamens, although some may produce small, soft pink to ivory-white, slightly recurved stamens 6 to 8 cm long.

Pollen and anthers: Most flowers have no anthers, but some may produce small, soft pink to ivory-white anthers which do not open.

Pistil: One in number, 6 to 8 cm long, ivory to very soft pink in color.

Stigma: RHS CC greyed purple 186 C, medium in size.

Characteristics of ovary: Characteristic of genus Lilium.

THE FRUIT

Fertility: The fruit bears fertile seed.

Shape: Ovoid.

Color at maturity: Soft brown, sometimes overlaid with soft plum.

My new variety of Asiatic hybrid lily most nearly resembles 'China,' but its flowers are more ruffled in appearance because of their "notched" inner tepals and occasional anther production. Its flowers are more red-pink and less purple-pink and are typically slightly more intense in color. It lacks the magenta hairline tepal margin of 'China.' It is much shorter than 'China,' with shorter, broader buds and shorter pedicels.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a pot-plant produced from pre-cooled bulbs forced under glass out of season; and in particular by its unusual double pink flowers with "notched" inner tepals, borne on exceptionally short stems, a combination unique among Asiatic hybrid lilies suited to forcing and to mass commercial cultivation.

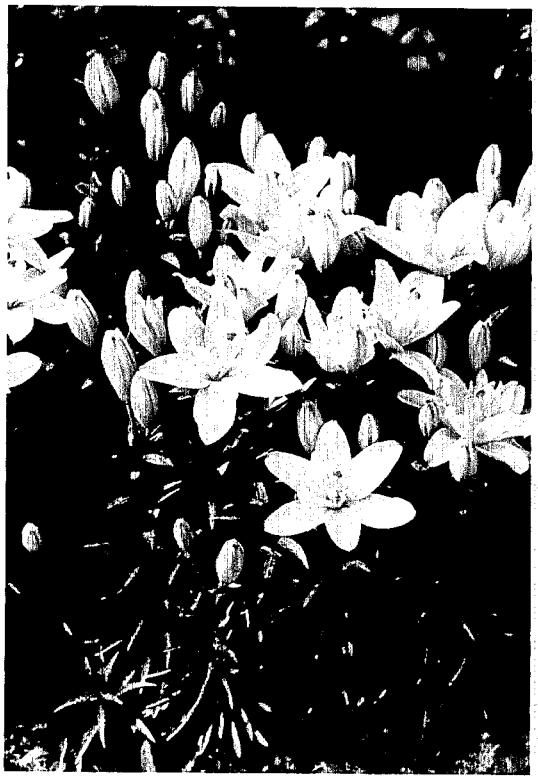
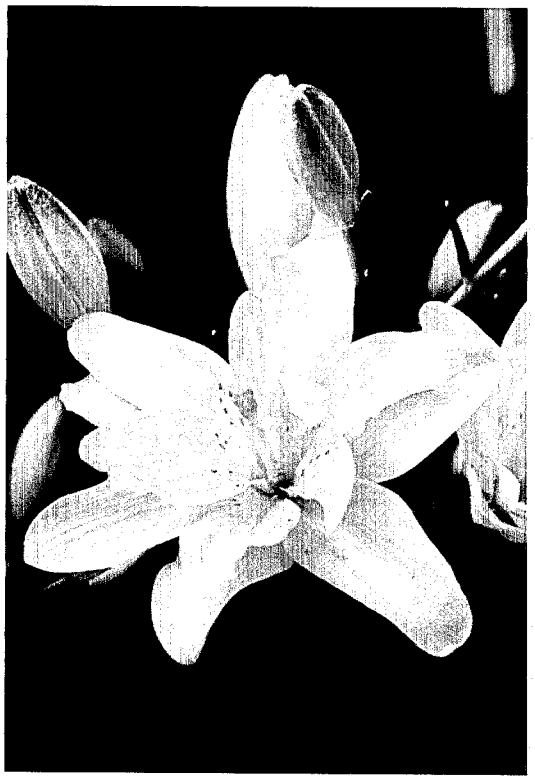
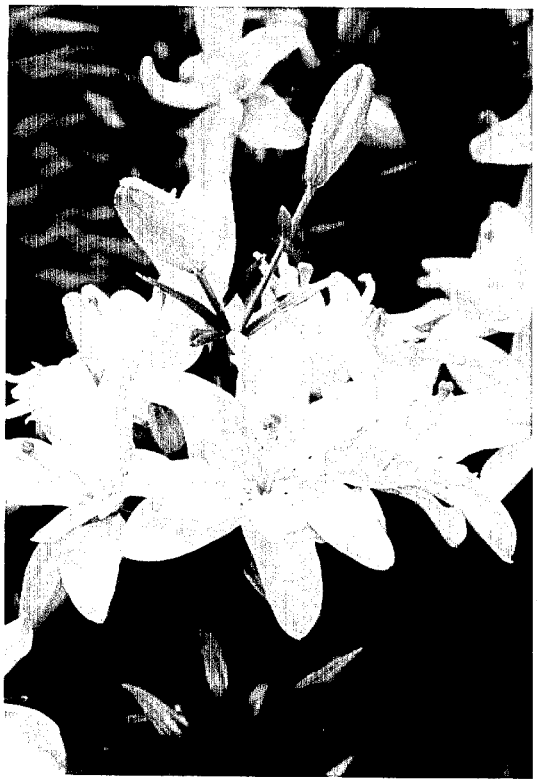

* * * * *